(12) United States Patent
Vadivelu (10) Patent No.: US 9,687,622 B2
(45) Date of Patent: Jun. 27, 2017

(54) MEDICAL APPARATUS WITH HYPOPHARYNGEAL SUCTIONING CAPABILITY

(75) Inventor: Nalini Vadivelu, Fairfield, CT (US)

(73) Assignee: AIRGUARD, LLC, Fairfield, CT (US)

( * ) Notice: Subject to any disclaimer, the term of this patent is extended or adjusted under 35 U.S.C. 154(b) by 1031 days.

(21) Appl. No.: 13/359,473

(22) Filed: Jan. 26, 2012

(65) Prior Publication Data

US 2012/0123393 A1    May 17, 2012

Related U.S. Application Data

(62) Division of application No. 11/817,606, filed as application No. PCT/US2006/010623 on Mar. 23, 2006, now Pat. No. 8,105,316.

(60) Provisional application No. 60/665,585, filed on Mar. 25, 2005.

(51) Int. Cl.
| | |
|---|---|
| *A61M 1/00* | (2006.01) |
| *A61M 16/04* | (2006.01) |
| *A61M 27/00* | (2006.01) |
| *A61M 37/00* | (2006.01) |
| *A61M 29/00* | (2006.01) |
| *A61M 5/14* | (2006.01) |
| *A61J 15/00* | (2006.01) |

(52) U.S. Cl.
CPC .... *A61M 16/0463* (2013.01); *A61M 16/0409* (2014.02); *A61M 16/0415* (2014.02); *A61J 15/0003* (2013.01); *A61J 15/0049* (2013.01); *A61J 15/0073* (2013.01)

(58) Field of Classification Search
CPC ........ A61M 1/00; A61M 27/00; A61M 37/00; A61M 29/00; A61M 5/14; A61M 5/00; A61M 5/315; A61F 5/44; A61F 2/00; A61F 2/02
See application file for complete search history.

(56) References Cited

U.S. PATENT DOCUMENTS

| | | | | | |
|---|---|---|---|---|---|
| 4,584,998 | A | * | 4/1986 | McGrail | 128/207.15 |
| 5,334,167 | A | * | 8/1994 | Cocanower | 604/523 |

* cited by examiner

*Primary Examiner* — Tatyana Zalukaeva
*Assistant Examiner* — Ilya Treyger
(74) *Attorney, Agent, or Firm* — Raymond A. Nuzzo (57) ABSTRACT

A medical apparatus having a nasogastric tube with hypopharyngeal suctioning capability. In one embodiment, the medical apparatus has a flexible nasogastric tube for insertion through a patient's nose. The nasogastric tube has a first end defining a first opening, a distal, second end that defines a second opening, and a length sufficient to allow the second opening to be positioned in a patient's stomach. The medical apparatus also has a flexible oropharyngeal tube for insertion through a patient's mouth. The oropharyngeal tube has a first end defining a first opening and a distal, second end that defines a suction intake. The oropharyngeal tube has a length that is less than the length of the nasogastric tube and which allows the suction intake to be positioned in a patient's hypopharynx region.

7 Claims, 12 Drawing Sheets

MEDICAL APPARATUS WITH HYPOPHARYNGEAL SUCTIONING CAPABILITY

CROSS-REFERENCE TO OTHER PATENT APPLICATIONS

This application is a divisional application of U.S. application Ser. No. 11/817,606, filed Aug. 31, 2007 now U.S. Pat. No. 8,105,316, which claims the benefit of international application No. PCT/US06/10623, filed Mar. 23, 2006, which claims the benefit of U.S. provisional application No. 60/665,585, filed Mar. 25, 2005. The entire disclosures of application Ser. No. 11/817,606 and 60/665,585 are hereby incorporated by reference.

BACKGROUND OF THE INVENTION

1) Field of the Invention

The present invention generally relates to nasogastric tubes and laryngeal masks.

2) Description of Prior Art

Nasogastric tubes and related devices are described in U.S. Pat. Nos. 5,643,230, 5,417,664, 5,011,474, 5,000,175, 4,821,715, 4,787,894, 4,735,607, 4,699,138, 4,508,533, and 4,214,593. Nasogastric tubes and related devices are also described in the following patents and published patent applications: EP 0500778, JP 10179677, WO 9716154, WO 9631248, and WO 8000538.

Nasogastric tubes are used to aspirate food contents from the stomach or to feed patients who are unable to safely feed themselves. Nasogastric tubes are commonly used in the operating room, intensive care units, home care, and in hospice settings. Prior art nasogastric tubes are frequently used to aspirate stomach contents. However, in some cases, aspiration of the stomach contents results in microaspirations which can cause nosocomial infections.

Similar problems can occur with prior art laryngeal masks. Laryngeal masks are used to provide ventilation and are commonly used in the operating room and in situations where it is difficult to insert an endotracheal tube. Prior art laryngeal masks and related devices are described in U.S. Pat. Nos. 4,351,328, 4,509,514, 4,995,388, 5,241,956, 5,303,697, 5,355,879, 5,632,271, 5,878,745, 6,631,720 and 6,895,966 and in published international patent application no. WO 1994/02191. A disadvantage of prior art laryngeal masks is that there is no protection from aspiration into the lungs of gastric contents or saliva regurgitated into the hypopharynx and pharynx.

SUMMARY OF THE INVENTION

The present invention is directed to, in one aspect, a medical apparatus comprising a nasogastric tube with hypopharyngeal suctioning capability. An important feature of the medical apparatus of the present invention is that it includes a suction intake in the area of the hypopharynx which effects capturing micro aspirations as well as larger regurgitated material that reaches the hypopharynx. A significant advantage of the present invention is that it reduces infection rates in intubated patients. In accordance with one embodiment of the invention, the medical apparatus comprises a flexible nasogastric tube for insertion through a patient's nose. The nasogastric tube has a first end and a distal, second end that defines an opening. The nasogastric tube has a length sufficient to allow the opening to be positioned in a patient's stomach. The medical apparatus further comprises a flexible oropharyngeal tube for insertion through a patient's mouth. The oropharyngeal tube has a first end and a distal, second end that defines a suction intake. The oropharyngeal tube has a length that is less than the length of the nasogastric tube and which allows the suction intake to be positioned in a patient's hypopharynx region. The medical apparatus further comprises a section of tube joined to and in communication with the flexible nasogastric and oropharyngeal tubes. The section of tube is configured to be joined to a suction apparatus that creates suction within the oropharyngeal tubes. This suction causes microaspirations and regurgitated material in the hypopharynx region to be sucked into the suction intake of the oropharyngeal tube.

In another aspect, the present invention is related to a medical apparatus comprising a laryngeal mask and a suction tube attached to the laryngeal mask. The suction tube includes a plurality of suction intakes that suck oropharyngeal secretions from the patient's mouth and the back of the patient's throat. Thus, in one embodiment, this medical apparatus comprises a laryngeal mask having a front side and rear side wherein the rear side faces the back of a patient's throat when the laryngeal mask is used in a patient, and a flexible suction tube attached to and extending along the rear side of the laryngeal mask. The suction tube comprises a plurality of suction intakes for suctioning oropharyngeal secretions in the patient's mouth and throat and has an opening that is configured to be connected to an apparatus for producing suction within the flexible suction tube.

BRIEF DESCRIPTION OF THE DRAWINGS

The features of the invention are believed to be novel. The figures are for illustration purposes only and are not drawn to scale. The invention itself may best be understood by reference to the detailed description which follows taken in conjunction with the accompanying drawings in which.

DETAILED DESCRIPTION OF THE INVENTION

Figure 1:
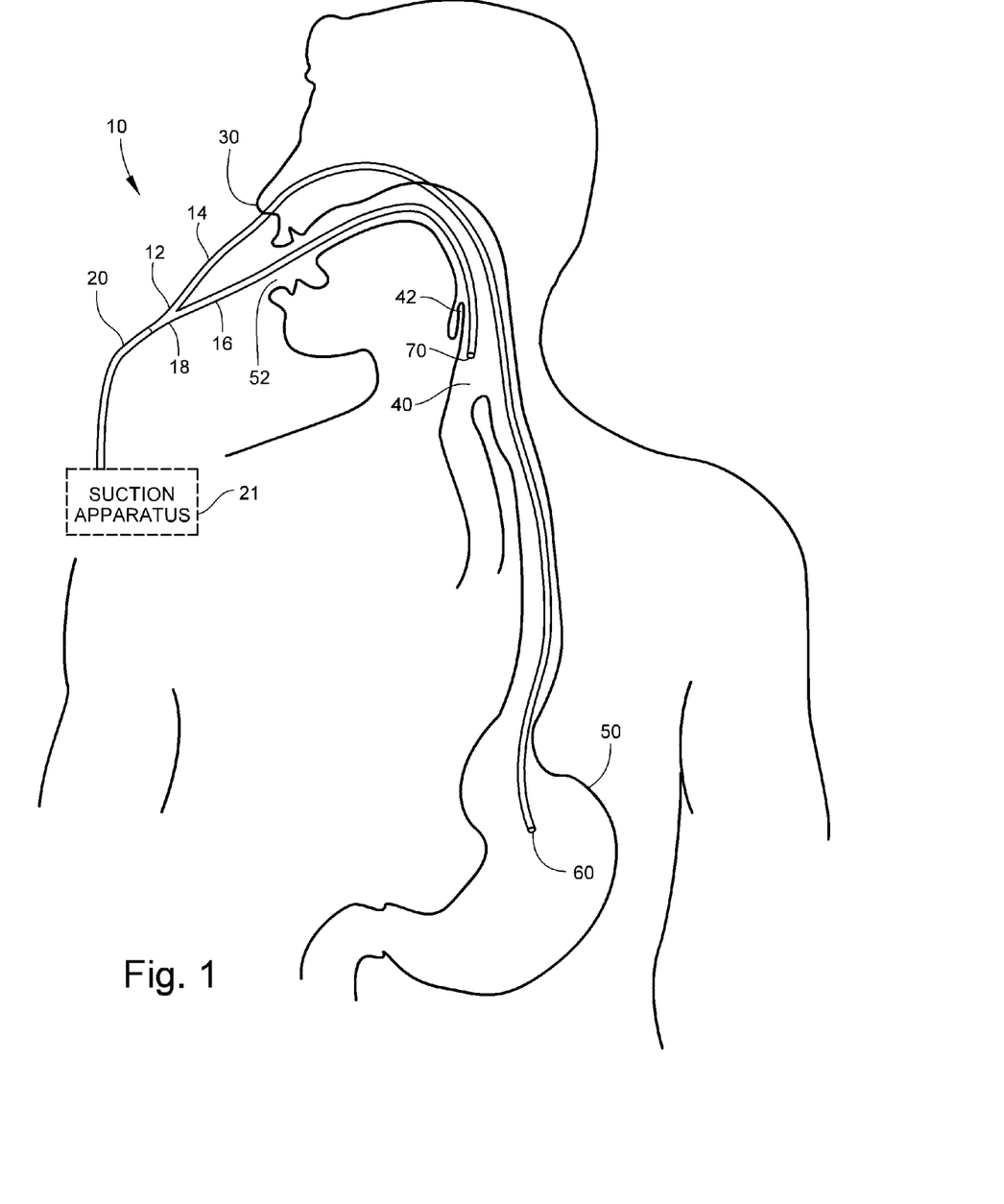
FIG. 1 is a diagrammatic view, generally in side elevation, of a medical apparatus in accordance with one embodiment of the invention, the same being shown used in a patient.

Referring to FIG. 1, there is shown a diagrammatic view of one embodiment of the medical apparatus of the present invention. This medical apparatus, generally indicated by reference numeral 10, comprises tube structure 12. Tube structure 12 comprises nasogastric tube section 14 and oropharyngeal tube section 16. The interior of nasogastric tube section 14 is known as the lumen. Similarly, the interior of oropharyngeal tube section 16 is known as the lumen. Nasogastric tube section 14 and oropharyngeal tube section 16 are joined together at tube section 18 so as to form a generally "Y" shaped configuration. Tube section 18 is configured to be connected to tube section 20. Tube section 20 is configured to be connected to an external apparatus 21 (shown in phantom). For example, such external apparatus 21 can be a suction apparatus for creating suction within tube structure 12. In another example, the aforesaid external apparatus can be a food source for feeding a patient that is unable to feed himself or herself.

As shown in FIG. 1, nasogastric tube section 14 has a sufficient length that allows it to be inserted through the patient's nose 30, through the hypopharynx region 40 (which is just below epiglottis 42) and into the patient's stomach 50. Nasogastric tube section 14 has opening 60 that is located in the patient's stomach 50. When tube section 20 is connected to suction apparatus 21, opening 60 functions as a suction intake that effects aspiration of food contents from the stomach. As a result of the suction, the aspirated food contents travel through nasogastric tube section 14 and into a container (not shown) in suction apparatus 21. On the other hand, if tube section 20 is connected to a food source, then opening 60 functions as an output for this food.

As shown in FIG. 1, oropharyngeal tube section 16 is inserted through the patient's mouth 52 and has a length that is relatively shorter than the length of nasogastric tube section 14. Oropharyngeal tube section 16 has suction intake 70. The length of oropharyngeal tube section 16 is such that suction intake 70 is positioned in hypopharynx region 40. When tube section 20 is connected to suction apparatus 21, suction intake 70 of oropharyngeal tube section 16 sucks in microaspirations and regurgitated material located in hypopharynx region 40 thereby removing such microaspirations and regurgitated material from hypopharynx region 40. Such microaspirations and regurgitated material travel through oropharyngeal tube section 16 and into the aforesaid container (not shown) in suction apparatus 21. Thus, suction intake 70 substantially reduces the risk of infection due to aspirations from the stomach 50 moving into the mouth 52.

In one embodiment, nasogastric tube section 14 and oropharyngeal tube section 16 are fabricated from commercially available flexible, soft plastic material, similar to the material used to fabricate conventional endotracheal tubes. In one embodiment, preferably, the internal diameter of such commercial plastic tubing is between about 5 mm and 10 mm.

Figure 2:
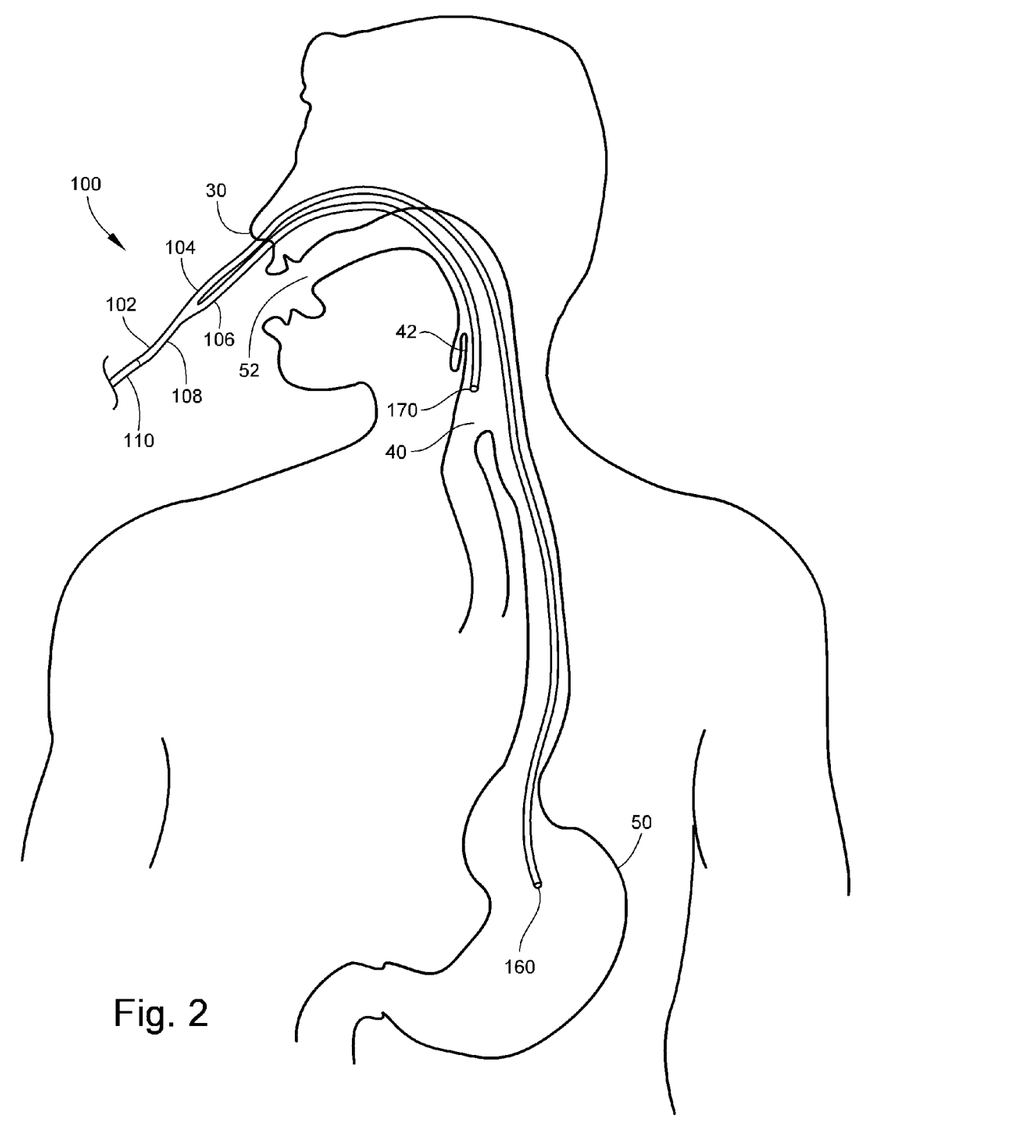
FIG. 2 is a diagrammatic view, generally in side elevation, of a medical apparatus in accordance with another embodiment of the invention, the same being shown used in a patient.

Referring to FIG. 2, there is shown medical apparatus 100 in accordance with another embodiment of the present invention. Medical apparatus 100 comprises tube structure 102. Tube structure 102 comprises nasogastric tube section 104, nasopharyngeal tube section 106, and tube section 108. Nasogastric tube section 104 and nasopharyngeal tube section 106 are joined together at tube section 108 so as to form a generally "Y" shaped configuration. Both nasogastric tube section 104 and nasopharyngeal tube section 106 are inserted through the patient's nose 30. Tube section 108 is configured to be connected to tube section 110. Tube section 110 is configured to be connected to an external apparatus (not shown). For example, such an external apparatus can be a suction apparatus such as suction apparatus 21 described in the foregoing description. Such a suction apparatus produces suction within tube structure 102. Thus, tube section 108 and tube section 110 have the same structure and perform the same functions as tube section 18 and tube section 20, respectively, of medical apparatus 10 described in the foregoing description. Nasogastric tube section 104 has opening 160. Nasogastric tube section 104 has a length that ensures that opening 160 is positioned in the patient's stomach 50. Nasogastric tube section 104 performs the same function as nasogastric tube section 14 (see FIG. 1). Nasopharyngeal tube section 106 has suction intake 170. Nasopharyngeal tube section 106 has a predetermined length that is less than the length of nasogastric tube section 104. This predetermined length of nasopharyngeal tube section 106 allows suction intake 170 to be positioned in the patient's hypopharynx region 40. Suction intake 170 performs the same function as suction intake 70 of oropharyngeal tube section 16 shown in FIG. 1. When the aforementioned suction apparatus is connected to tube section 110, suction intake 170 sucks in microaspirations and regurgitated material located in hypopharynx region 40 thereby removing such microaspirations and regurgitated material in hypopharynx region 40. Thus, suction intake 170 substantially reduces the risk of infection due to aspirations from stomach 50 moving into mouth 52.

Figure 3A:
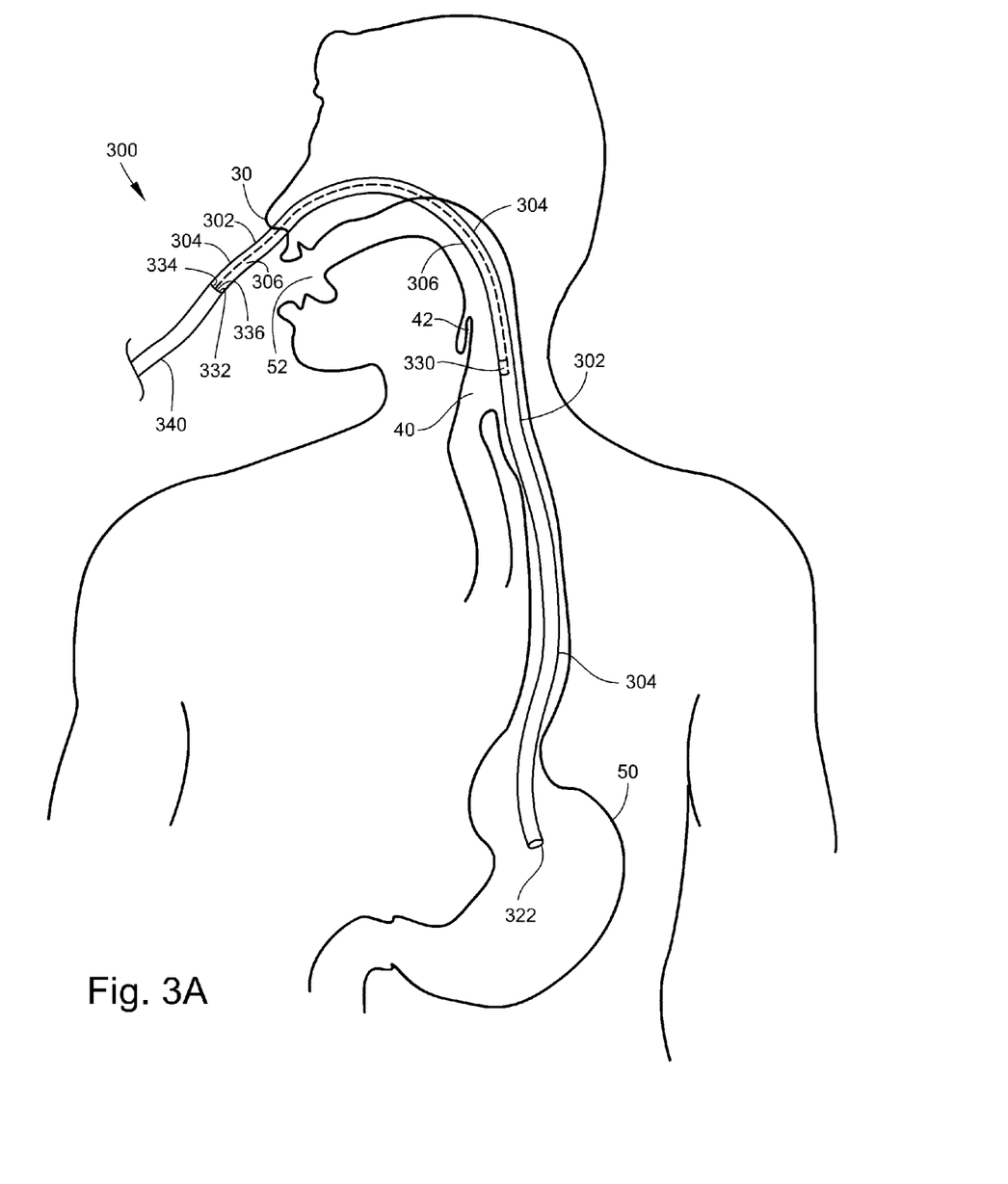
FIG. 3A is a diagrammatic view, generally in side elevation, of a medical apparatus in accordance with another embodiment of the invention, the same being shown used in a patient.
Figure 3B:
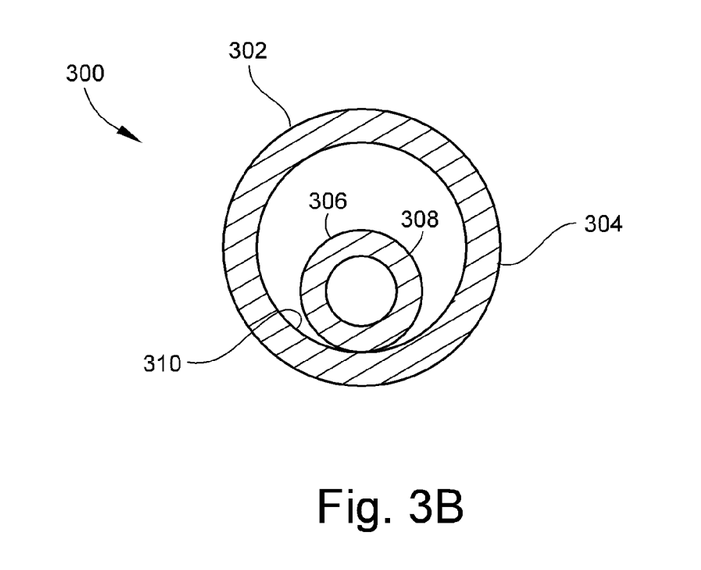
FIG. 3B is a cross-sectional view of the tube structure shown in FIG. 3A.
Figure 3C:
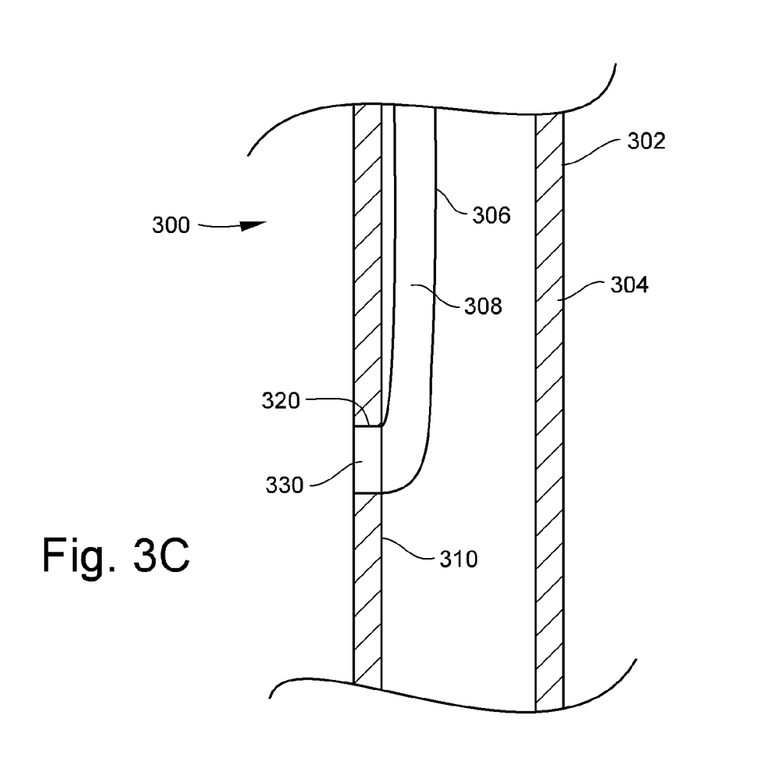
FIG. 3C is an enlarged view of a portion of the view of FIG. 3A.
Figure 3D:
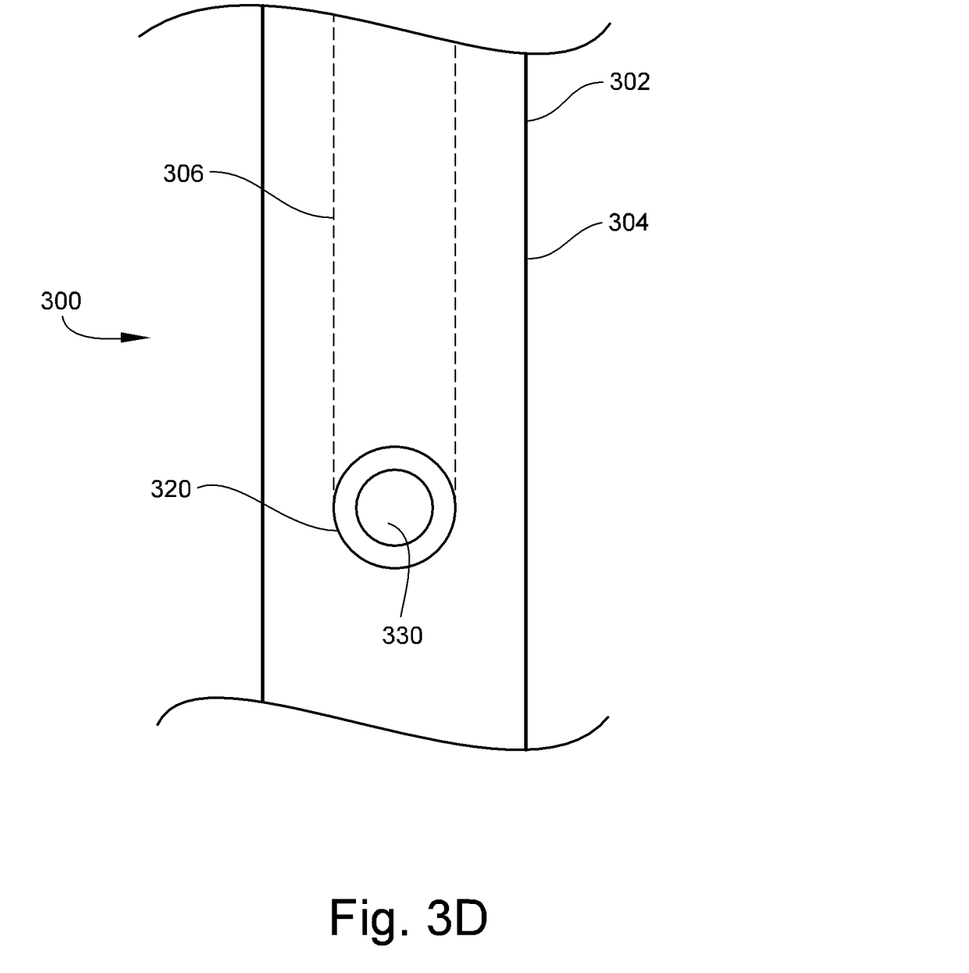
FIG. 3D is an elevational view of a portion of the tube structure shown in FIG. 3A.

Referring to FIGS. 3A-D, there is shown medical apparatus 300 in accordance with a further embodiment of the present invention. Medical apparatus 300 comprises tube structure 302 which is configured to be inserted through the patient's nose 30. Tube structure 302 comprises an outer tube 304 and an inner conduit 306. Thus, inner conduit 306 is positioned within outer tube 304. In one embodiment, as shown in FIG. 3B, inner conduit 306 is a tube having an outer surface 308. In such an embodiment, outer surface 308 is attached to inner surface 310 of outer tube 304. In another embodiment, inner conduit 306 is integrally formed with outer tube 304 during the manufacture of tube structure 302. Outer tube 304 includes openings 320 and 322. The length of outer tube 304 is such that opening 322 is located in the patient's stomach 50. Opening 322 serves the same purpose as opening 60 (see FIG. 1) and opening 160 (see FIG. 2). As shown in FIGS. 3A and 3C, the length of inner conduit 306 is less than the length of outer tube 304. Tube structure 302 has a predetermined length that allows opening 320 to be located in the patient's hypopharynx region 40. Inner conduit 306 includes opening 330 that is aligned and in communication with opening 320 in outer tube 304. Opening 330 functions as a suction intake port or opening. Referring to FIG. 3A, tube structure 302 has end 332. Outer tube 304 has opening 334 adjacent to end 332. Inner conduit 306 has opening 336 adjacent to end 332. Medical apparatus 300 includes tube section 340 that is joined to end 332 of tube structure 302. Tube section 340 serves the same purpose as tube section 20 (see FIG. 1) and is configured to be connected to an external apparatus such as suction apparatus 21 described in the foregoing description. When a suction apparatus is connected to tube section 340, suction is produced within tube structure 302 which results in microaspirations and regurgitated material located in hypopharynx region 40 to be sucked into opening 330. Thus, microaspirations and regurgitated material in hypopharynx region 40 are removed thereby substantially reducing the risk of infection due to aspirations from stomach 50 moving into mouth 52.

The medical apparatus shown in FIGS. 1-3D provide many important advantages. One such advantage is that the suction intake in hypopharynx region 40 captures microaspirations as well as relatively larger regurgitated material and particles that enter the hypopharynx. This feature reduces the risk of infection due to aspirations from the stomach moving into the mouth. This medical apparatus can be used during surgery for patients with any of the following conditions:
 a) gastric obstruction;
 b) gastroesophageal reflux disease (GERD);
 c) diabetes patients who have full stomachs;
 d) pregnancy (enlarged abdomens and at risk for aspiration);
 e) cancer patients (poor digestion, enlarged abdominal tumors, and/or vomiting); and
 f) patients on medications that increase incidence of nausea and vomiting.

This medical apparatus also can be used in the ICU (Intensive Care Unit) for patients in any of the following situations:
 a) intubated patients who have increased risk of microaspiration in the presence of a nasogastric tube and an endotracheal tube, such as patients with bowel obstruction;
 b) patients with total parental nutrition who are not intubated but require a nasogastric tube to prevent aspiration; and
 c) patients who have gastroparesis, cancer, diabetes, pregnancy and other conditions where patients have a full stomach and require a nasogastric tube.

In accordance with another embodiment of the invention, medical apparatus 400, shown in FIGS. 4-7, is an improved laryngeal mask configured to effect suctioning the hypopharynx region. Medical apparatus 400 comprises laryngeal mask 402 and suction tube 404. In a preferred embodiment, laryngeal mask 402 is configured as the laryngeal mask described in U.S. Pat. No. 4,509,514, the disclosure of which is hereby incorporated by reference. Laryngeal mask 402 has a front side 406 and rear side 408. Suction tube 404 is located at the rear side 408 of laryngeal mask 402. In one embodiment, suction tube 404 is integrally formed with laryngeal mask 402 during the manufacture of medical apparatus 400. In another embodiment, suction tube 404 is a separate component that is attached to the rear side 408 of laryngeal mask 400. In such an embodiment, any suitable technique can be used to attach suction tube 404 to rear side 408 of laryngeal mask 400. Laryngeal mask 402 comprises flexible breathing tube 410 and mask portion 412 with an inflatable tubular ring 414. Inflatable tubular ring 414 has distal end 415. Suction tube 404 is preferably fabricated from soft plastics material, similar to that conventionally used for endotrachael tubes. Suction tube 404 comprises a rear side that is attached to rear side 408 of laryngeal mask 402. Suction tube 404 includes front side 422. Suction tube 404 further includes tube sections 430 and 440 that are joined together at middle tube section 450. Sections 430 and 440 are attached to the rear side of mask portion 412. Suction tube 404 further includes tube section 460 that is connected to middle tube section 450 and extends along the rear side of flexible breathing tube 410. Each tube section 430 and 440 has a plurality of suction ports 470 formed on front side 422. Suction tube 404 has end portion 480 that defines opening 482. End portion 480 is configured to be connected to a suction hose (not shown) that is connected to an external suction apparatus (not shown) such as suction apparatus 21 described in the foregoing description.

Figure 7:
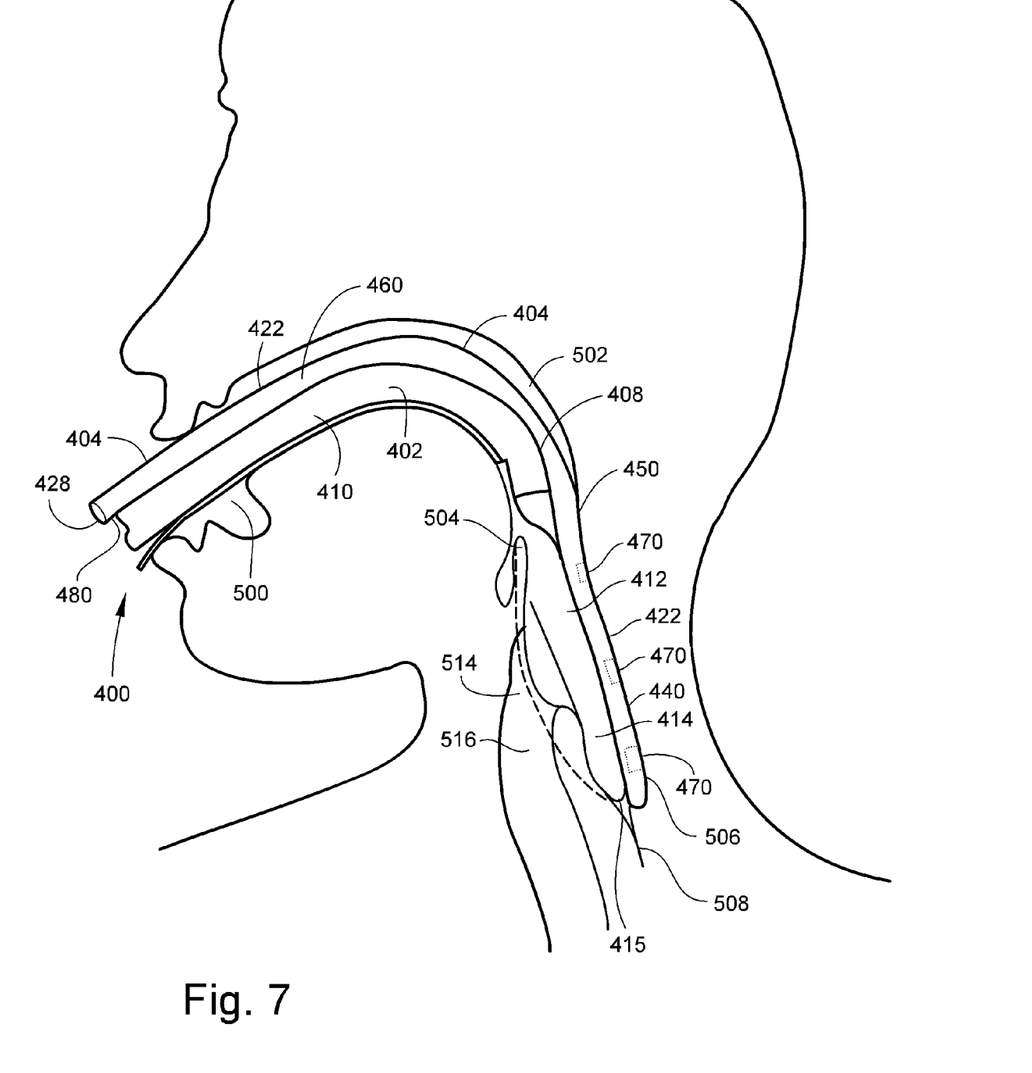
FIG. 7 is a diagrammatic view of the medical apparatus of FIG. 4 used in a patient.

Referring to FIG. 7, when in use, medical apparatus 400 is inserted into the patient's mouth 500 and down through the patient's throat 502 past the epiglottis 504 until mask portion 412 comes to rest with distal end 415 of inflatable ring 414 in the base 506 of throat 502, lying against the upper end of the normally closed esophagus 508. Suction ports 470 face the back of throat 502. Inflatable ring 414 is then inflated as shown to seal around inlet 514 to larynx 516. The patient's airway is thus secure and unobstructed and flexible tube 410 is then connected directly to the conventional anesthetic circuit hosing for either positive pressure or spontaneous breathing. End portion 480 of suction tube 404 is then connected to a suction apparatus to allow suction ports 470 to suck oropharyngeal secretions from the mouth and the back of the throat 502. Such secretions are made not only from the patient's stomach, but also from the salivary glands in the mouth.

Figure 4:
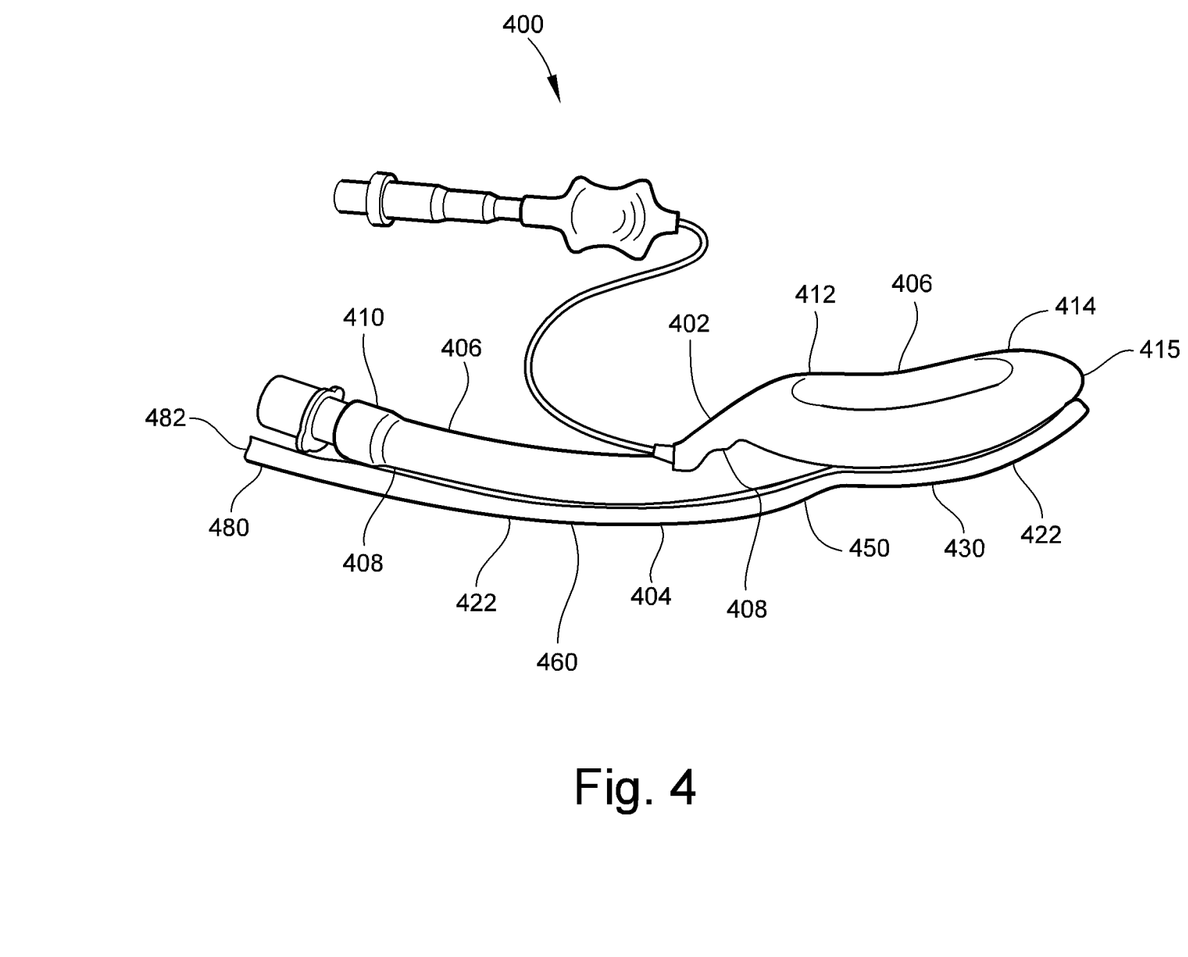
FIG. 4 is a perspective view of a medical apparatus in accordance with another embodiment of the invention.
Figure 5:
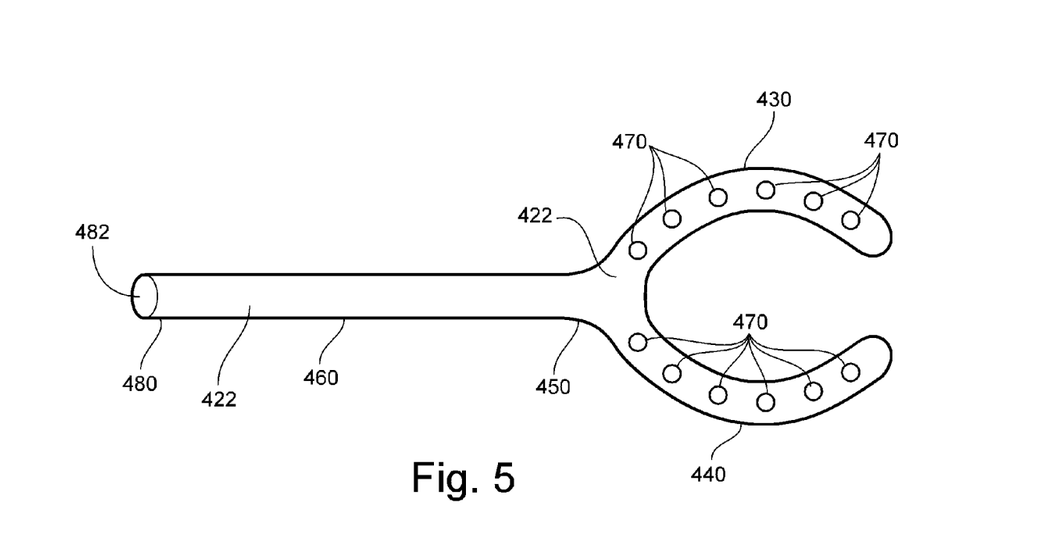
FIG. 5 is a plan view of the front side of a suction tube depicted in FIG. 4.
Figure 6:
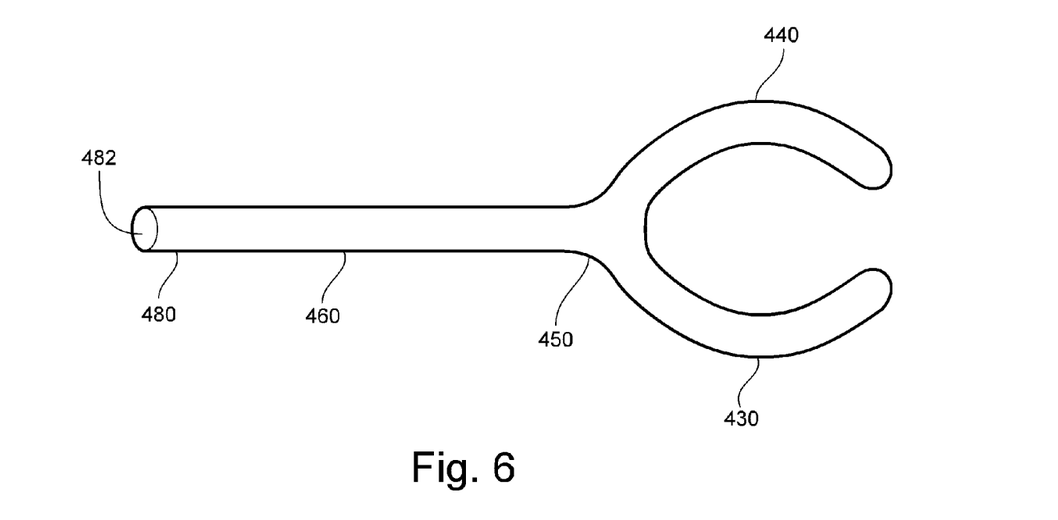
FIG. 6 is a plan view of the rear side of the suction tube shown in FIG. 5.

Medical apparatus 400 provides a laryngeal mask with increased versatility which can be used in many situations including patients with the following conditions:
 a) gastroesophageal reflux disease;
 b) gastric obstruction;
 c) diabetes with full stomachs;
 d) pregnancy (enlarged abdomen and at risk of aspiration);
 e) cancer (poor digestion, enlarged abdomen, nausea/vomiting)

Figure 8:
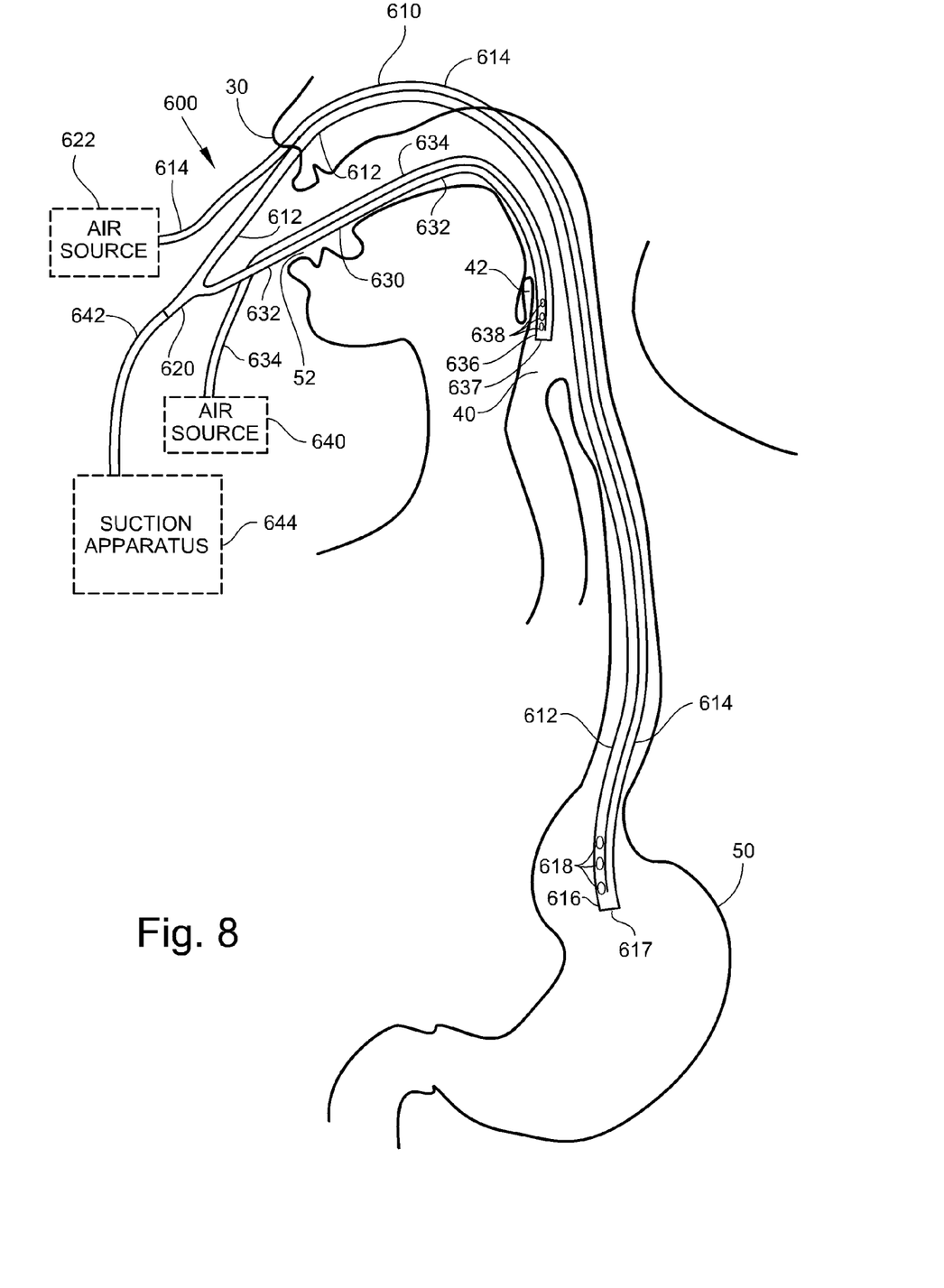
FIG. 8 is a diagrammatic view, generally in side elevation, of a medical apparatus in accordance with a further embodiment of the invention, the same being shown used in a patient.
Figure 9:
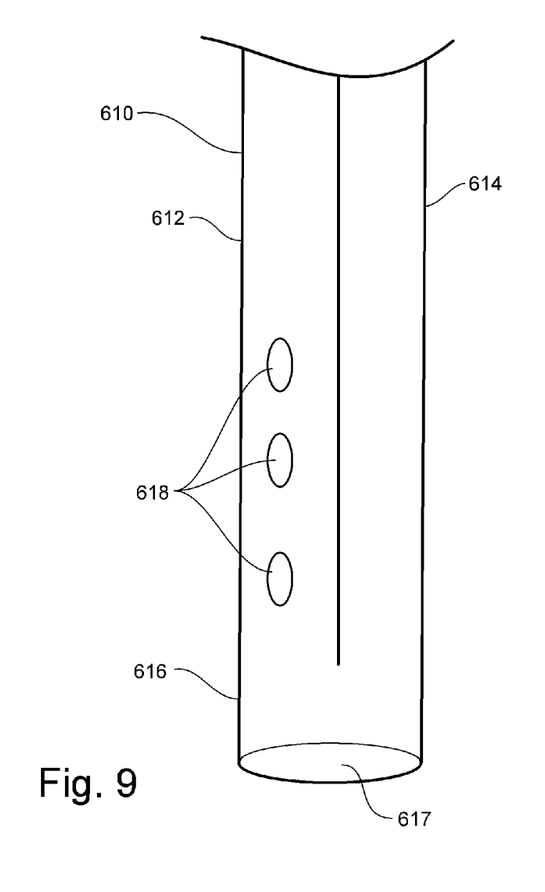
FIG. 9 is an enlarged view of a portion of the view shown in FIG. 8.
Figure 10:
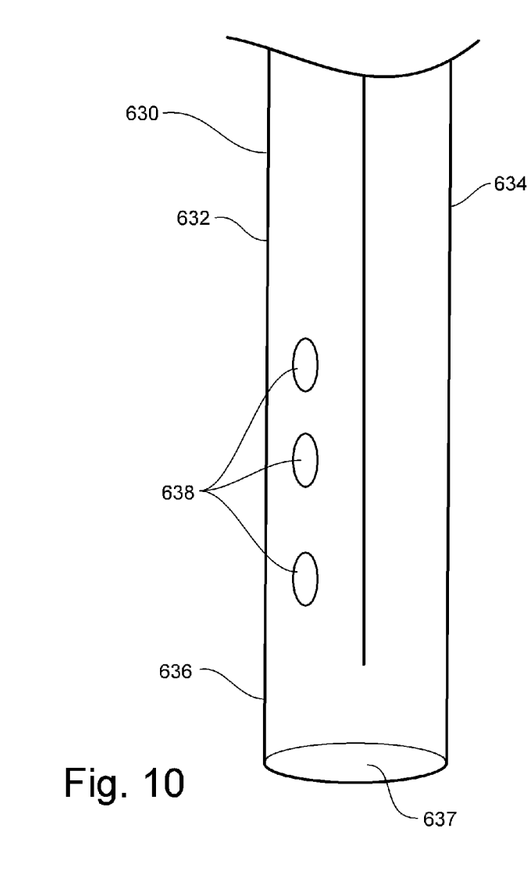
FIG. 10 is an enlarged view of a portion of the view shown in FIG. 8.

Referring to FIGS. 8, 9 and 10, there is shown medical apparatus 600 in accordance with another embodiment of the invention. Medical apparatus 600 is configured for the situation wherein continuous suction is necessary. As will be shown by the ensuing discussion, medical apparatus 600 prevents collapse of the hypopharynx and stomach walls while continuous suctioning is occurring and also prevents damage to stomach and hypopharynx tissues. Medical apparatus 600 generally comprises nasogastric tube structure 610. Nasogastric tube structure 610 comprises suction tube 612 and air tube 614. Suction tube 612 and air tube 614 are joined together at end portion 616. End portion 616 defines opening 617. Opening 617 is in communication with suction tube 612 and air tube 614. In one embodiment, the portions of suction tube 612 and air tube 614 that extend from end portion 616 are attached together until they exit the patient's body. The length of nasogastric tube structure 610 is such that end portion 616 is positioned in stomach 50. Suction tube 612 has suction intakes 618. Suction tube 612 and air tube 614 separate outside of the patient's body in order to allow these two tubes to be connected to separate medical equipment. Suction tube 612 is joined to tube section 620 and air tube 614 is joined to air source 622.

Medical apparatus 600 further comprises oropharyngeal tube structure 630. Oropharyngeal tube structure 630 includes suction tube 632 and air tube 634 which are joined at end portion 636. End portion 636 defines opening 637. Oropharyngeal tube structure 630 includes suction intakes 638. Oropharyngeal tube structure 630 has a predetermined length that is shorter than the length of tube structure 610 thereby allowing end portion 636 to be positioned in hypopharynx region 40. The portions of suction tube 632 and air tube 634 that extend from end portion 636 are attached together until these tubes exit the patient's body. Suction tube 632 is joined to tube section 620. Air tube 634 is connected to air source 640. Tube section 620 is joined to intermediate tube section 642. Intermediate tube section 642 is connected to a suction apparatus 644. Air source 622 provides air to air tube 614. This air exits air tube 614 at opening 617. Air source 640 provides air to air tube 634. Such air exits air tube 634 at opening 637 in tube structure 630. Suction apparatus 644 produces suction within suction tubes 612 and 632. As a result of such suction, stomach contents are sucked into suction intakes 618 and microaspirations and regurgitated material and particles in hypopharynx region 40 are sucked through section intakes 638. The air in air tube 614 prevents collapse of the stomach 50 and prevents suction intakes 618 from contacting and sucking the stomach walls. Thus, damage to the tissues of the stomach wall and mucosa is prevented. Similarly, the air in air tube 634 enters hypopharynx region 40 and prevents a collapse of the hypopharynx. This air also prevents suction intakes 638 from contacting and damaging the walls and tissues of the hypopharynx.

If low-level, continuous suctioning is needed in stomach 50 and high-level, continuous suctioning is needed in the hypopharynx, then air source 622 can be inactivated while air source 640 continues to provide air to air tube 634. Similarly, if low-level, continuous suctioning is needed in hypopharynx region 40 and high-level, continuous suctioning is needed in stomach 50, then air source 622 is activated and air source 640 is inactivated.

In another embodiment, nasogastric tube structure 610 is configured so that suction tube 612, air tube 614 and end portion 616 are integral with each other. Similarly, in another embodiment, oropharyngeal tube structure 630 is configured so that suction tube 632, air tube 634 and end portion 636 are integral with each other. In a further embodiment, nasogastric tube structure 610 is configured so that the air tube (e.g. air tube 614) is positioned inside the suction tube (e.g. suction tube 612). Similarly, in a further embodiment, oropharyngeal tube structure 630 is configured so that its air tube (e.g. air tube 634) is positioned within the suction tube (e.g. suction tube 632).

Figure 11:
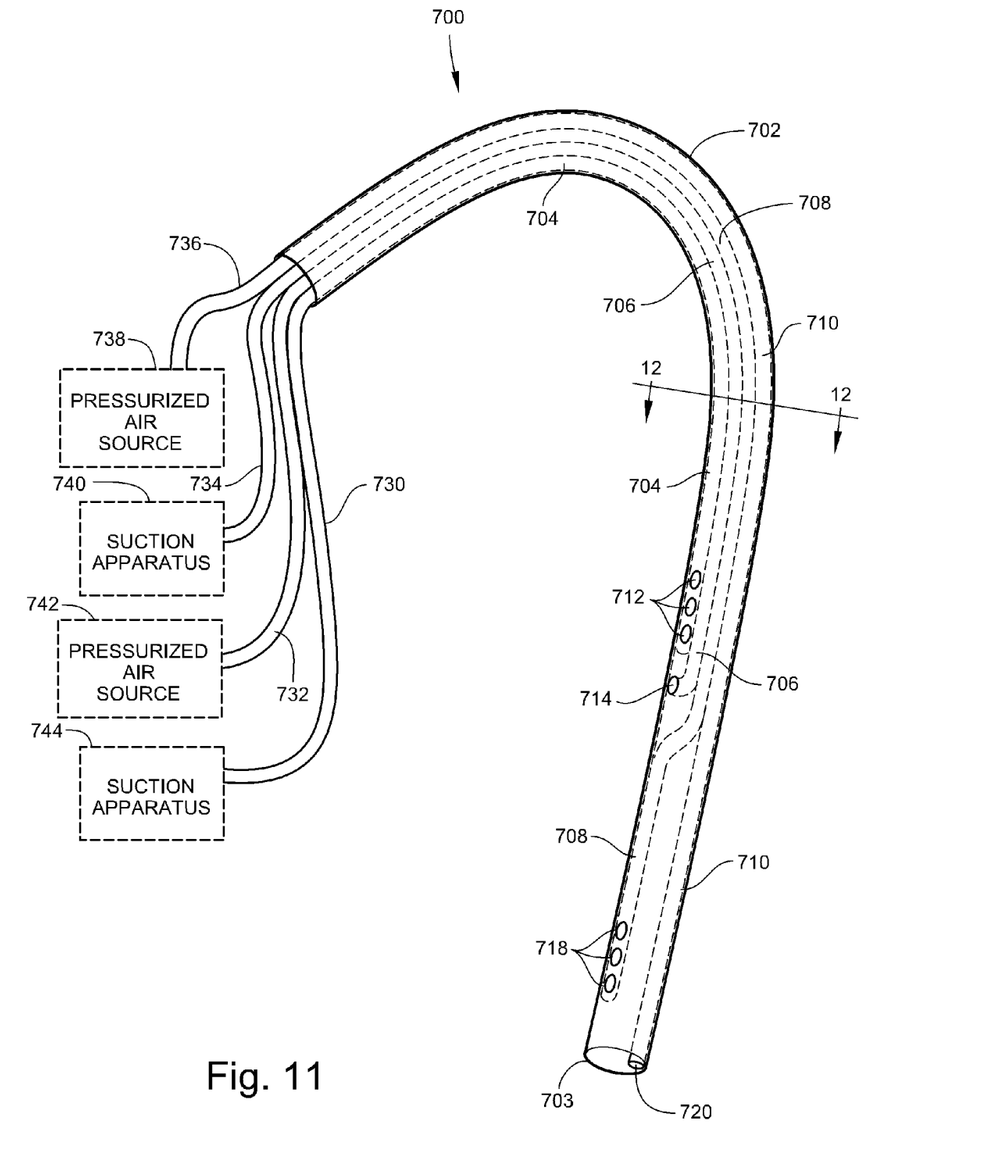
FIG. 11 is an elevational view of a medical apparatus in accordance with another embodiment of the invention.
Figure 12:
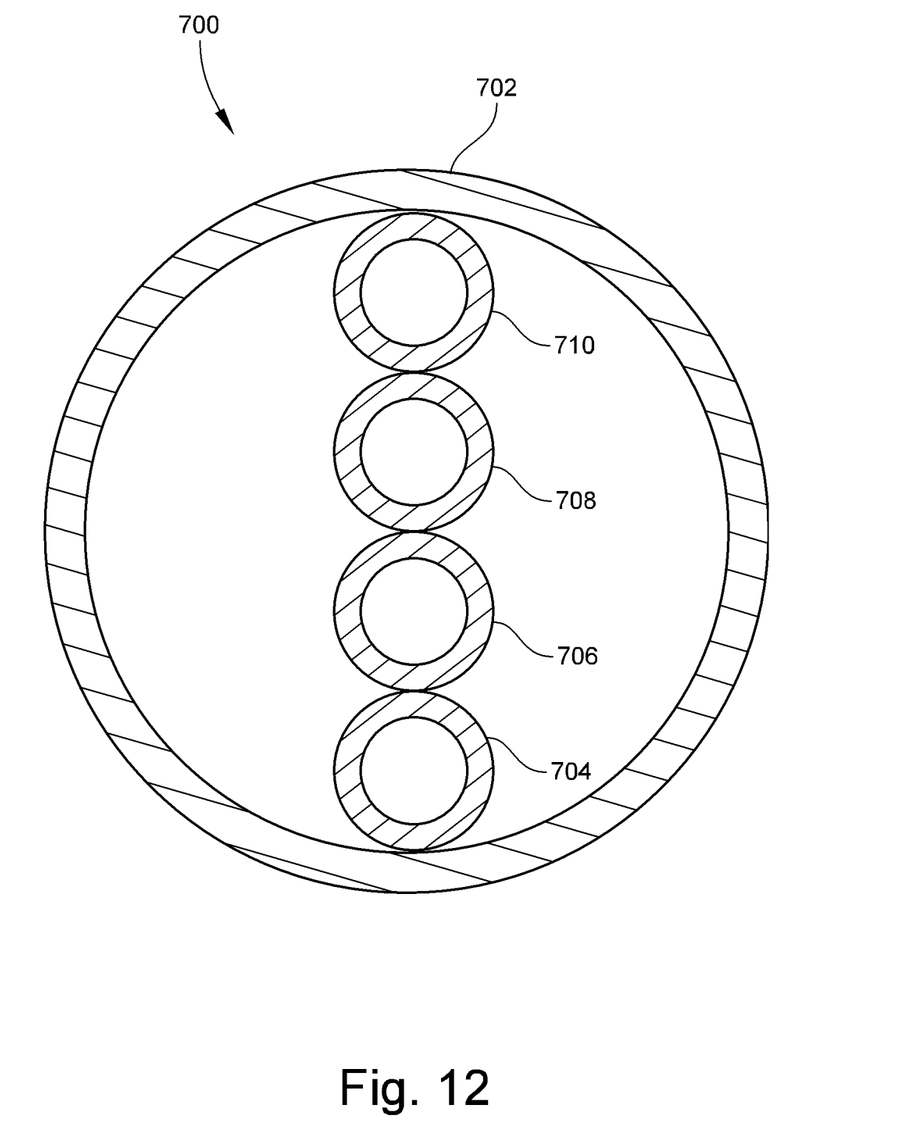
FIG. 12 is a cross-sectional view taken along line 12-12 in FIG. 11.

Referring to FIGS. 11 and 12, there is shown medical apparatus 700 in accordance with another embodiment of the invention. As with medical apparatus 600, medical apparatus 700 is configured for use in the situation wherein continuous high-level suctioning is necessary. As will be shown by the ensuing discussion, medical apparatus 700 prevents collapse of the hypopharynx and stomach walls while continuous suctioning is occurring and also prevents damage to stomach and hypopharynx tissues. Medical apparatus 700 comprises outer tube 702 which is configured to be inserted either through a patient's mouth or patient's nose. Tube 702 has a distal end 703 and a predetermined length that allows end 703 to be positioned in a patient's stomach. Tube 702 comprises four separate conduits 704, 706, 708 and 710 which are not in communication with each other. Conduits 704 and 708 are suction conduits. Conduits 706 and 710 are air conduits. Tube 702 includes suction intakes or openings 712 that are in communication with suction conduit 704. Suction intakes 712 are located a predetermined location along the length of tube 702 that corresponds to the hypopharynx region of a patient when tube 702 is inserted in a patient. When suction is applied to suction conduit 704, microaspirations and regurgitated material in the hypopharynx region are sucked through suction intakes 712 and up through conduit 704 and into an external suction apparatus as will be explained in the ensuing description. Tube 702 includes an opening or vent 714. Air conduit 706 is in communication with opening 714. When pressurized air is provided to air conduit 706, such air is vented through opening 714. The purpose of this configuration is explained in the ensuing discussion. Tube 702 also includes suction intakes or openings 718. Suction conduit 708 is in communication with suction intakes 718. When suction is applied to suction conduit 708, stomach contents are sucked through suction intakes 718 and up through suction conduit 708 and into an external suction apparatus as will be explained in the ensuing description. As shown in FIG. 11, air conduit 710 has opening or vent 720. When pressurized air is supplied to air conduit 710, the pressurized air vents through opening 720 and into the patient's stomach.

Referring to FIG. 11, medical apparatus 700 further comprises tube sections 730, 732, 734 and 736. Tube section 730 is joined to and in communication with conduit 704. Tube section 732 is joined to and in communication with conduit 706. Tube section 734 is joined to and in communication with conduit 708. Tube section 736 is joined to and in communication with conduit 710. Tube section 730 is configured to be connected to suction apparatus 744. Tube section 732 is configured to be connected to pressurized air source 742. Tube section 734 is configured to be connected to suction apparatus 740. Tube section 736 is configured to be connected to pressurized air source 738. Suction apparatuses 740 and 744 are separate apparatuses. In one scenario, one suction apparatus can provide high-level suction while the other suction apparatus can provide low-level suction. In another scenario, both suction apparatuses provide low-level suction. In a further scenario, both suction apparatuses provide high-level suction. Pressurized air sources 738 and 742 are separate air sources and each has an activated state and an inactivated state. Thus, both pressurized air sources can be activated, inactivated, or one pressurized source activated and the other pressurized air source inactivated.

When tube 702 is inserted into a patient and high-level suction of the stomach and hypopharynx is necessary, suction apparatuses 744 and 740 produce suction within suction conduits 704 and 708, respectively. Stomach contents are sucked into suction intakes 718, and micro aspirations and regurgitated material in the hypopharynx region are sucked into suction intakes 712. All material sucked into suction intakes 712 and 718 are sucked through conduits 704 and 708, respectively, and into baskets or other containers inside suction apparatuses 744 and 740, respectively. In order to prevent suction intakes 712 and 718 from damaging tissues in the hypopharynx and stomach, respectively, pressurized air sources 742 and 738 provide air to air conduits 706 and 710, respectively. The pressurized air supplied to air conduit 706 is vented through opening 714 and the pressurized air provided to air conduit 710 is vented through opening 720. As a result, the pressurized air vented through opening 714 keeps suction intakes 712 away from hypopharynx tissue, and the pressurized air vented through opening 720 keeps suction intakes 718 away from stomach tissue. If high-level suctioning is needed in the hypopharynx but only low-level suctioning is needed in the stomach, then pressurized air source 738 can be inactivated while pressurized air source 742 remains activated. Similarly, if low-level suctioning is needed in the hypopharynx but high-level suctioning is needed in the stomach, then pressurized air source 742 can be inactivated while pressurized air source 738 remains activated.

In one embodiment, each conduit 704, 706, 708 and 710 is configured as a tube. In another embodiment, conduits 704, 706, 708 and 710 are integrally formed with tube 702 during the manufacturing process.

In one embodiment, tube 702 and conduits 704, 706, 708 and 710 are fabricated from the same materials used to fabricate the tubes of the medical apparatuses described in the foregoing description.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the invention. Accordingly, the foregoing detailed description should be considered as exemplary in nature and not as limiting the scope and spirit of the invention as set forth in the attached claims.

What is claimed is:

1. A medical apparatus (600) for simultaneously suctioning contents in a patient's stomach (50) and suctioning microaspirations, regurgitated material and particles in the patient's hypopharyngeal region (40), comprising:
    a flexible nasogastric tube structure (610) for insertion through a patient's nose comprising an end portion (616) which has an opening (617), the flexible nasogastric tube structure (610) having a predetermined length that allows opening (617) to be positioned in a patient's stomach (50), the flexible nasogastric tube structure (610) further comprising:
        a flexible suction tube section (612) having a portion thereof outside the patient's nose and at least one suction intake (618) in proximity to the end portion (616), wherein the predetermined length of the flexible nasogastric tube structure (610) allows the at least one suction intake (618) to be positioned in a patient's stomach 50,
        a flexible air tube section (614) having a portion thereof that is outside the patient's nose and adapted for connection to an air source (622); and
        wherein the opening (617) is in communication with both flexible suction tube section (612) and flexible air tube section (614);
    a flexible oropharyngeal tube structure (630) for insertion into a patient's mouth comprising an end portion (636) which has an opening (637), the flexible oropharyngeal tube structure (630) having a predetermined length that allows opening (637) to be positioned in a patient's hypopharynx region (40), the flexible oropharyngeal tube structure (630) further comprising:
        a flexible suction tube section (632) having a portion thereof that is outside the patient's mouth, the flexible suction tube section (632) having at least one second suction intake (638) in proximity to the end portion (637), wherein the predetermined length of the flexible oropharyngeal tube structure (630) allows the at least one suction intake (638) to be positioned in a patient's hypopharynx region (40), and
        a flexible air tube section (634) having a portion thereof that is outside of the patient's mouth and adapted for connection to an air source (640), and
        wherein the opening (637) is in communication with both flexible suction tube section (632) and flexible air tube section (634); and
    a tube section (620) joined to the portion of the flexible suction tube section (612) that is outside the patient's nose and to the portion of the flexible suction tube section (632) that is outside the patient's mouth, the tube section (620) having an opening adapted for connection to a suction apparatus (644) so as to allow suction to be produced in the flexible suction tube section (612) and in flexible suction tube section (632) simultaneously; and
    whereby when suction is produced in the tube section (620) and air is provided to flexible air tube sections (614) and (634), the patient's stomach contents are sucked into the at least one suction intake (618) and microaspirations and particles in the patient's hypopharynx region (40) are sucked into the at least one suction intake (638) and air exiting opening (617) prevents collapse of the stomach (50) and also prevents the at least one suction intake (618) from contacting and sucking the stomach walls and the air exiting opening (637) enters the hypopharynx region (40) to prevent collapse of the hypopharynx and also prevent the at least one suction intake (638) from contacting and damaging the walls and tissues of the hypopharynx.

2. The medical apparatus (600) according to claim 1 further comprising a suction apparatus (644) connected to the opening of the tube section (620) to produce suction in flexible suction tube sections (612) and (632) simultaneously.

3. The medical apparatus (600) according to claim 2 further comprising a first air source (622) that is connected to the portion of the flexible air tube section (614) that is outside the patient's nose and a second air source (640) that is connected to the portion of flexible air tube section (634) that is outside the patient's mouth in order to introduce air into air tube sections (614) and (634).

4. A medical apparatus (700) for simultaneously suctioning contents in a patient's stomach (50) and suctioning microaspirations, regurgitated material and particles in the patient's hypopharyngeal region (40), comprising:
    a flexible outer tube (702) for insertion through a patient's mouth (52) or nose (30) comprising a first end having a first tube opening and an opposite distal, second end (703) having a second tube opening, the flexible outer tube (702) having at least one lower suction intake (718) and at least one intermediate suction intake (712) that is located between the first tube opening and the lower suction intake (718), the flexible outer tube (702) having an opening (714) in proximity to the intermediate suction intake (712), the flexible outer tube (702) having a predetermined length that allows (i) the first end to extend from the patient's mouth (52) or nose (30), (ii) the lower suction intake (718) to be positioned in a patient's stomach (50), and (iii) the intermediate suction intake (712) to be positioned within the hypopharynx region (40) of a patient;
    a first inner suction conduit (704) disposed within the flexible outer tube (702) and having a first end portion that extends from the first tube opening of the flexible outer tube (702) and an opposite second end portion that is positioned adjacent to the at least one intermediate suction intake (712), the first inner conduit (704)

having at least one opening aligned and in communication with the at least one intermediate suction intake (712);

a first inner air conduit (706) disposed within the flexible outer tube (702) and having a first end portion that extends from the first tube opening of the flexible outer tube (702) and an opposite second end portion that has an opening that is in communication with opening (714) of the flexible outer tube (702);

a second inner suction conduit (708) disposed within the flexible outer tube (702) and having a first end portion that extends from the first tube opening of the flexible outer tube (702) and an opposite second end portion that has at least one opening that is in communication with the at least one suction intake (718) of the flexible outer tube (702);

a second inner air conduit (710) disposed within the flexible outer tube (702) and having a first end portion that extends from the first tube opening of the flexible outer tube (702) and an opposite second end portion that has an opening that is in proximity to end (703) of the flexible outer tube (702); and whereby when suction is produced in the first inner suction conduit (704) and in the second inner suction conduit (708) and pressurized air is delivered to first inner air conduit (706) and to second inner air conduit (710), the patient's stomach contents are sucked into the at least one suction intake (718) and microaspirations and particles in the patient's hypopharynx regions (40) are sucked into the at least one intermediate suction intake (712) and air exiting opening (720) prevents collapse of the stomach (50) and prevents suction intakes (718) from contacting and sucking the stomach walls and the pressurized air exiting opening (714) enters the hypopharynx region (40) so as to prevent collapse of the hypopharynx and prevent the at least one intermediate suction intake (712) from contacting and damaging the walls and tissues of the hypopharynx.

5. The medical apparatus (700) according to claim 4 further comprising:

a first suction producing apparatus (744) for producing suction within first inner air conduit (704) so as to cause microaspirations and regurgitated material in the hypopharynx region (40) to be sucked into the at least one intermediate suction intake (712);

a second suction apparatus (740) for producing suction within the second inner suction conduit (708) so as to cause stomach contents to be sucked into the at least one lower suction intake (718);

a first pressurized air source (742) to deliver pressurized air to the first inner air conduit (706) such that pressurized air exits the opening (714) and enters the hypopharynx region (40) so as to prevent collapse of the hypopharynx and prevent the at least one intermediate suction intake (712) from contacting and damaging the walls and tissues of the hypopharynx; and a second pressurized air source (738) to deliver pressurized air to the second inner air conduit (710) such that pressurized air exits opening (720) so as to prevent the at least one suction intake (718) from contacting and sucking the stomach walls.

6. A medical apparatus (300) for simultaneously suctioning contents in a patient's stomach (50) and suctioning microaspirations, regurgitated material and particles in the patient's hypopharyngeal region (40), comprising a flexible nasogastric tube (302) configured for insertion through a patient's nose (30) and comprising a first end having a suction intake (322) and an opposite second end having an opening for connection to a suction producing apparatus, the flexible nasogastric tube (302) having an opening (320) that is located between the suction intake (322) and the opposite second end, the flexible nasogastric tube (302) having a predetermined length such that when the nasogastric tube (302) is inserted into a patient, the opening (320) is positioned in a patient's hypopharyngeal region (40) and the suction intake (322) is positioned in a patient's stomach (50), the nasogastric tube (302) having an inner suction conduit (306) disposed within the flexible nasogastric tube (302) and having an end that defines an opening (330) that is aligned and in communication with opening (320) in the flexible nasogastric tube (302), the inner suction conduit (306) including an opposite end having an opening that is within the opening of the opposite second end of the flexible nasogastric tube (302) such that when a suction apparatus is connected to the opening of the opposite second end of the flexible nasogastric tube (302), suction is created within both the flexible nasogastric tube (302) and the inner suction conduit (306) which causes suction intake (322) to suck in stomach contents and opening (330) of inner suction conduit (302) to suck in microaspirations and regurgitated material located in hypopharynx region (40).

7. The medical apparatus (300) according to claim 6 further comprising a suction producing apparatus to produce suction within flexible nasogastric tube (302) and the inner suction conduit (306).

* * * * *